(12) United States Patent
Blackburn et al.

(10) Patent No.: US 7,193,350 B1
(45) Date of Patent: Mar. 20, 2007

(54) ELECTROACTIVE POLYMER STRUCTURE

(75) Inventors: Michael R. Blackburn, Encinitas, CA (US); Selahattin Ozcelik, Corpus Christi, TX (US)

(73) Assignee: United States of America as Represented by the Secretary of the Navy, Washington, DC (US)

( * ) Notice: Subject to any disclaimer, the term of this patent is extended or adjusted under 35 U.S.C. 154(b) by 198 days.

(21) Appl. No.: 11/066,377

(22) Filed: Feb. 25, 2005

(51) Int. Cl.
*H01L 41/08* (2006.01)

(52) U.S. Cl. ...................... 310/311; 310/328
(58) Field of Classification Search .............. None
See application file for complete search history.

(56) References Cited

U.S. PATENT DOCUMENTS

2003/0212356 A1* 11/2003 Scorvo .................... 602/20
2005/0245853 A1* 11/2005 Scorvo .................... 602/16

FOREIGN PATENT DOCUMENTS

CA 2466711 * 4/2003
CA 2466496 * 12/2003

* cited by examiner

Primary Examiner—Thomas M. Dougherty
(74) Attorney, Agent, or Firm—Allan Y. Lee; Michael A. Kagan; Peter A. Lipovsky

(57) ABSTRACT

An electroactive polymer (EAP) structure. The structure includes at least one EAP strand. An EAP strand includes a plurality of EAP segments and a plurality of insulators. An EAP segment includes an EAP tile and an activator. The activator facilitates activation of the EAP tile. The plurality of EAP segments and the plurality of insulators have a concatenated configuration, wherein adjacent EAP segments are electrically separated by one of the plurality of insulators, and wherein the EAP segments are operatively coupled to the plurality of insulators. A method for the system is also described.

13 Claims, 7 Drawing Sheets

Top View

400

400

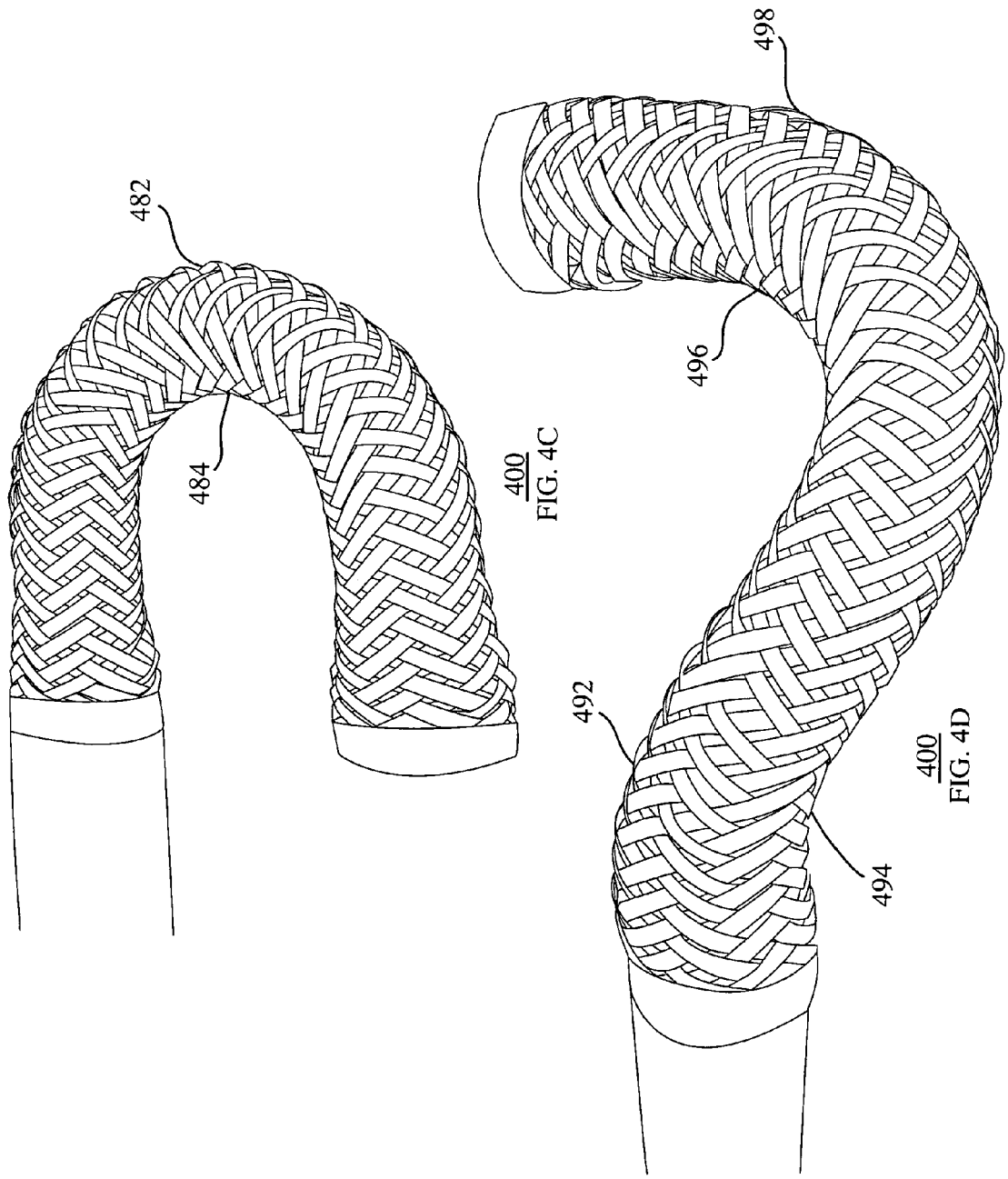

ELECTROACTIVE POLYMER STRUCTURE

BACKGROUND

The patent application is generally in the field of electroactive polymer (EAP) structures.

Typical EAP structures include EAP attached to fixed frames, which result in bulky, heavy structures. Typical EAP structures also include EAP bladders, which have poor local control over shape.

A need exists for EAP structures having decreased bulk and mass. In addition, a need exists for EAP structures having increased flexibility and local control over shape.

BRIEF DESCRIPTION OF THE DRAWINGS

FIG. 4C is a side view of one embodiment of an EAP structure.

FIG. 4D is a side view of one embodiment of an EAP structure.

DETAILED DESCRIPTION

Electroactive Polymer Structures are described herein.

Glossary

The following definitions and acronyms are used herein:

Acronym(s):

EAP—Electroactive Polymer

Definition(s):

Activator—facilitate activation of electroactive polymers

Braid Angle—angle that forms between two overlapping strands of a braided structure The EAP structure includes a concatenated plurality of EAP segments that form an EAP strand, wherein each EAP segment is electrically isolated from other EAP segments and can be individually controlled. In one embodiment, the EAP structure includes a plurality of strands that are braided to form an EAP braided structure, which can selectively deform by activating individual EAP segments or specified groups of EAP segments. In one embodiment, the EAP structure comprises a biaxial braid. Examples of EAP structures include a snake, a ball, a plate and an animal-shaped toy. In one embodiment, the EAP structure has decreased bulk and mass. In one embodiment, the EAP structure has increased flexibility. In one embodiment, the EAP structure has increased local control over shape. By assembling EAP strands into braided structures, EAP segments of EAP strands can cooperate to move the braided structure, both locally and globally, and apply directed forces upon the internal or external environments. A braided structure can distribute forces across both surfaces of overlapping EAP segments. In addition, a braided structure permits EAP segments to shift spatial relationships to achieve deformations of the global braided structure, and then to renormalize spatial relationships when forces are removed.

Figure 1:
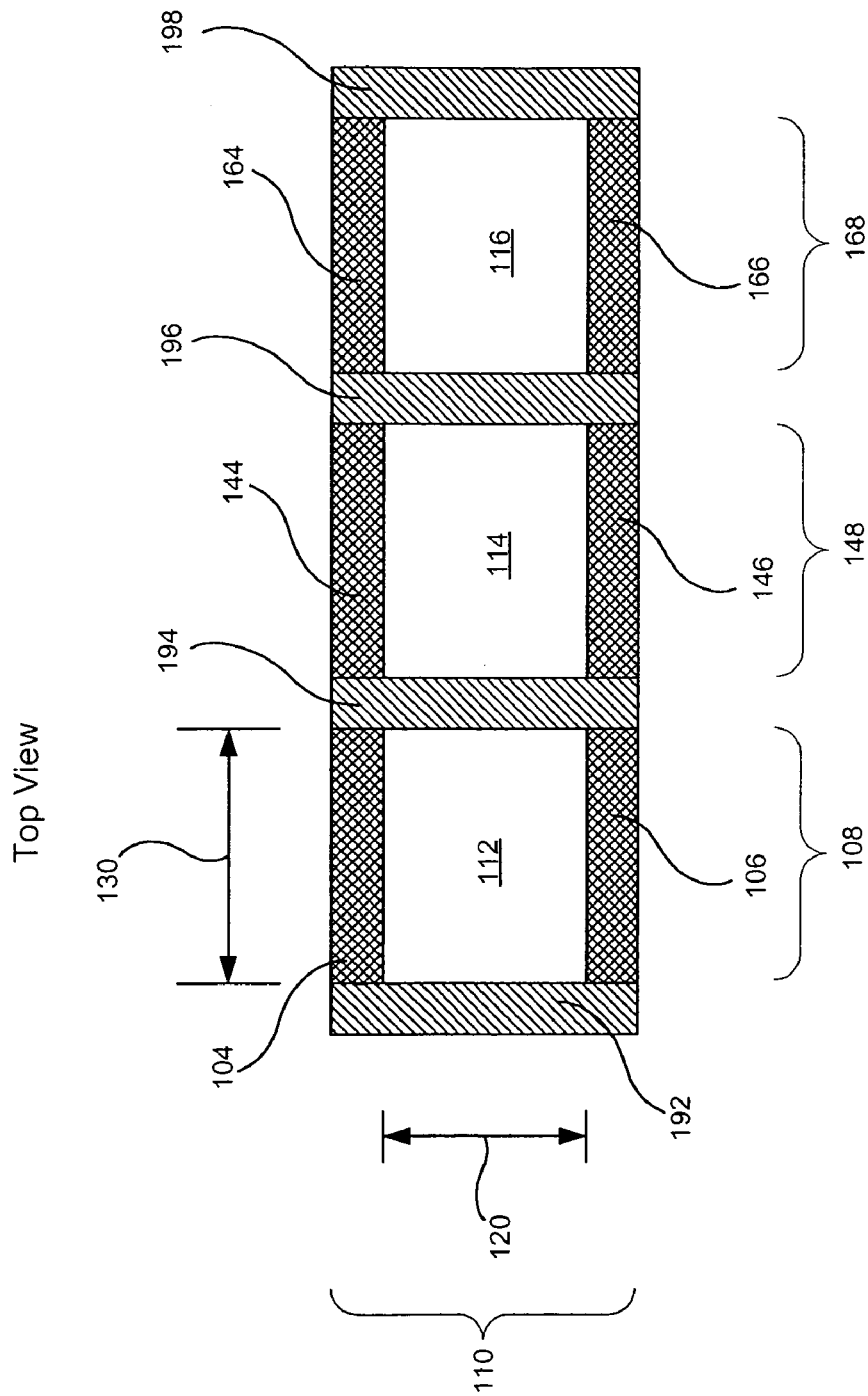
FIG. 1 is a top view of one embodiment of an EAP structure.

FIG. 1 is a top view of one embodiment of an EAP structure. FIG. 1 shows an EAP strand embodiment. The EAP strand includes a concatenated plurality of EAP segments that are separated by insulators. As shown in FIG. 1, EAP strand 110 includes EAP segments 108, 148, 168 and insulators 192, 194, 196, 198. Insulators 192, 194, 196, 198 comprise nonconductive material such as plastic. Insulator 194 electrically isolates EAP tile 112 and EAP tile 114; and insulator 196 electrically isolates EAP tile 114 and EAP tile 116.

EAP segments include EAP tiles and activators (e.g., first electrodes and second electrodes). Activators facilitate activation of EAP tiles. EAP segment 108 includes EAP tile 112, first electrode 104 and second electrode 106; EAP segment 148 includes EAP tile 114, first electrode 144 and second electrode 146; and EAP segment 168 includes EAP tile 116, first electrode 164 and second electrode 166. EAP tile 112 has width 120 and length 130. Width 120 and length 130 are substantially greater than the depth of EAP tile 112. EAP tile 112 comprises electroactive polymer material. In one embodiment, EAP tile 112 comprises conductive polymers. Exemplary conductive polymers include polypyrroles, polyanilines, polyacetylenes, polyethyldioxithiophenes, and polythiophenes. In one embodiment, EAP tile 112 comprises dielectric elastomers. Exemplary dielectric elastomers include Dow Corning HS3 silicone, Nusil CF 19-2186 silicone, and 3M VHB 4910 acrylic. Those skilled in the art shall recognize that actuators other than EAP such as, for example, ferroelectric polymers, liquid crystal elastomers, carbon nanotube actuators, ionic polymer metal composites, can be used with the EAP structure without departing from the scope or spirit of the EAP structure.

First electrodes 104, 144, 164 and second electrodes 106, 146, 166 comprise conductive material such as, for example, metal, semiconductor, conductive fluid, conductive polymer, photonic charge release material and a combination thereof. First electrodes 104, 144, 164 and second electrodes 106, 146, 166 can be used to activate EAP tiles 112, 114, 116. Specifically, first electrode 104 and second electrode 106 can be used to activate EAP tile 112; first electrode 144 and second electrode 146 can be used to activate EAP tile 114; and first electrode 164 and second electrode 166 can be used to activate EAP tile 116. In one embodiment, EAP tile 112 deforms when first electrode 104 and second electrode 106 have different voltage potentials. In one embodiment, phase and potential can be changed to obtain a great diversity of motion. A controller (not shown in FIG. 1) can be operatively coupled to first electrodes 104, 144, 164 and second electrodes 106, 146, 166 to individually control voltage potentials between these electrodes. Thus, EAP tiles 112, 114, 116 can be activated individually or in groups because first electrodes 104, 144, 164 and second electrodes 106, 146, 166 can be controlled individually. In one embodiment, EAP strand 110 is encased in a conductive polymer.

A plurality of EAP strands can be configured into an EAP structure. Those skilled in the art shall recognize that an EAP structure can comprise numerous configurations without departing from the scope or spirit of the EAP structure. Exemplary EAP structures include EAP biaxial braids, EAP biaxial braided snakes, EAP braided spheres, EAP braided discs, EAP braided artificial muscles, EAP braided regulators (e.g., artificial sphincter), EAP braided peristaltic pumps (e.g., artificial heart, esophagus and colon) and EAP braided locally controllable bladders. A plurality of discrete EAP structures can be configured to produce a complex EAP structure. Exemplary complex EAP structures include EAP animal toys having discrete EAP structures for limbs, torso and head, which can all be activated independently or in conjunction.

Figure 2A:
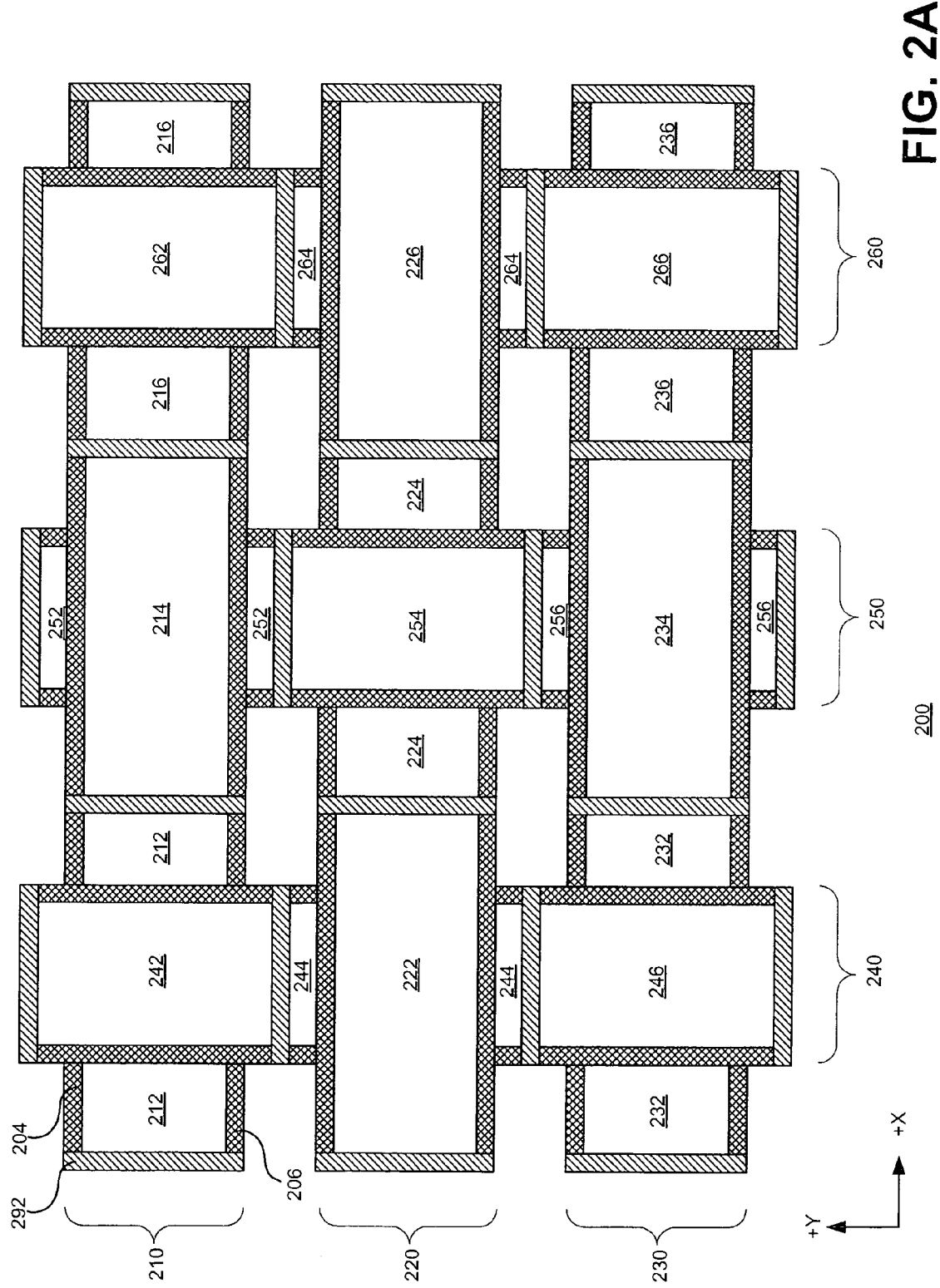
FIG. 2A is a top view of one embodiment of an EAP structure.

FIG. 2A is a top view of one embodiment of an EAP structure. EAP braided structure 200 includes a plurality of EAP strands having a braided configuration. EAP braided structure 200 of FIG. 2A has a "one-over, one-under" braided configuration. Those skilled in the art shall recognize that other braided configurations such as a "two-over, one-under, two-under, one-over" braided configuration can be used with EAP braided structure 200 without departing from the scope or spirit of EAP braided structure 200. As shown in FIG. 2A, EAP braided structure 200 includes EAP strands 210, 220, 230, 240, 250, 260, which are substantially similar to EAP strand 110 of FIG. 1, and thus, are not described in detail hereinagain. EAP strand 210 includes EAP tiles 212, 214, 216, first electrode 204, second electrode 206 and insulator 292, which are analogous to EAP tiles 112, 114, 116, first electrode 104, second electrode 106 and insulator 192 of EAP strand 110 of FIG. 1. EAP strand 220 includes EAP tiles 222, 224, 226; EAP strand 230 includes EAP tiles 232, 234, 236; EAP strand 240 includes EAP tiles 242, 244, 246; EAP strand 250 includes EAP tiles 252, 254, 256; EAP strand 260 includes EAP tiles 262, 264, 266. The braid angle between overlapping EAP strands (e.g., EAP strands 230, 240) is approximately equal to 90 degrees. A controller (not shown in FIG. 2A) can be operatively coupled to the first and second electrodes of EAP tiles 212, 214, 216, 222, 224, 226, 232, 234, 236, 242, 244, 246, 252, 254, 256, 262, 264, 266 to individually control voltage potentials between these electrodes. Thus, EAP tiles of EAP braided structure 200 can be activated individually or in groups to selectively deform EAP braided structure 200.

Figure 2B:
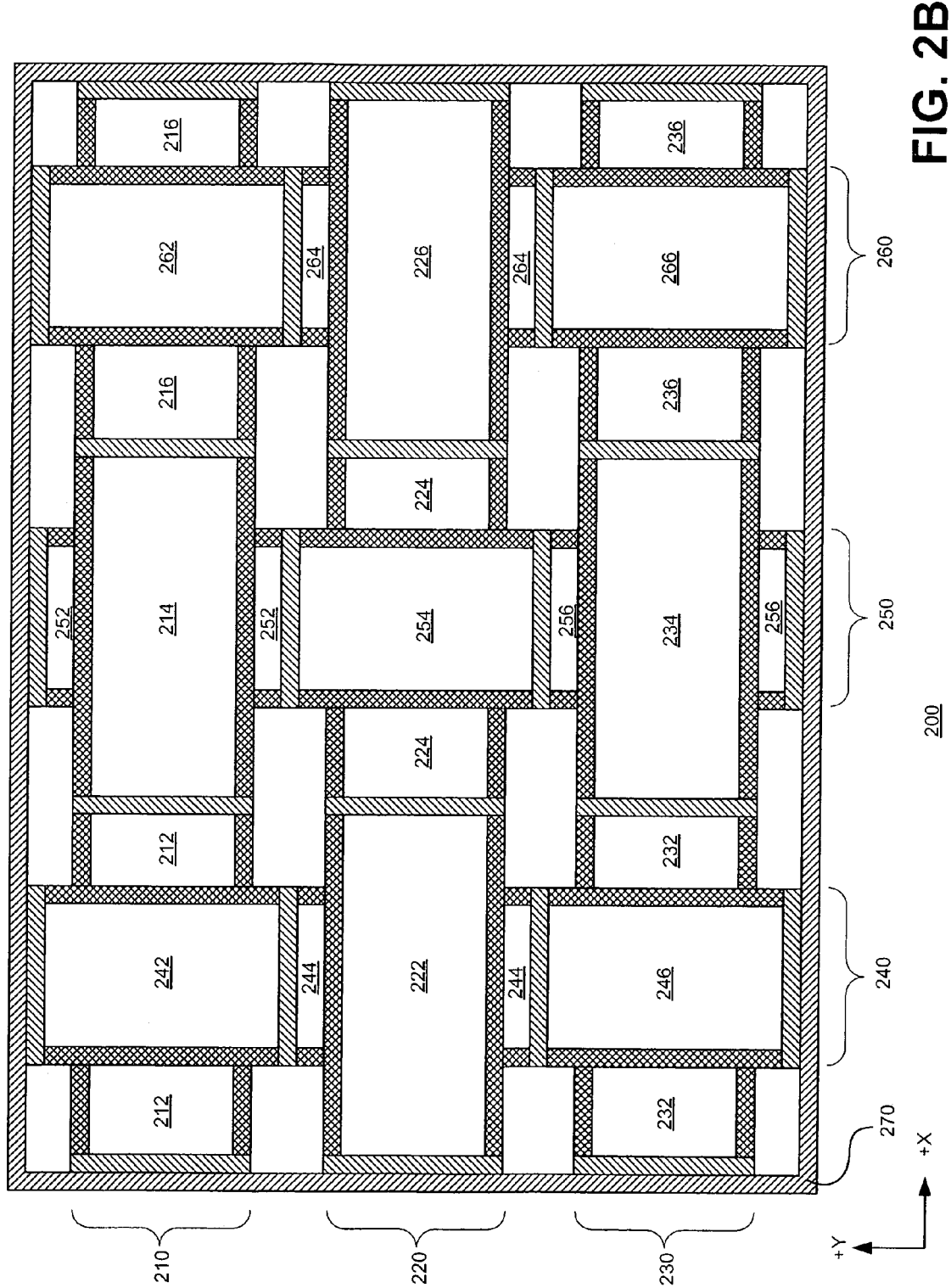
FIG. 2B is a top view of one embodiment of an EAP structure.

FIG. 2B is a top view of one embodiment of an EAP structure. As shown in FIG. 2B, EAP structure 200 includes frame 270. Frame 270 is operatively coupled to ends of EAP strands 210, 220, 230, 240, 250, 260. Frame 270 can comprise rigid or elastic material. In one embodiment, frame 270 comprises a rigid material such as, for example, plastic, composite and metal. In one embodiment, frame 270 comprises an elastic frame such as, for example, rubber.

As shown in FIG. 2B, EAP strands are braided so that EAP tiles overlap (e.g., EAP tile 254 overlaps EAP tile 224). This braided configuration allows EAP tiles to operate in conjunction to provide desired deformations or motions. Exemplary operation of EAP braided structure 200 is now described. Activating EAP tiles in opposite directions provides a rigid area. For example, activating EAP tile 226 in the −Z direction (i.e., into FIG. 2B) and activating EAP tile 264 in the +Z direction (i.e., away from FIG. 2B) provides a rigid area where EAP tile 226 and EAP tile 264 overlap. Activating EAP tiles in the same direction provides a hump or dip. For example, activating EAP tiles 234, 256 in the +Z direction forms a hump where EAP tiles 234, 256 overlap. In another example, activating EAP tiles 222, 244 in the −Z direction forms a dip where EAP tiles 222, 244 overlap. EAP tiles form pliable areas, which can be deformed by external forces. Activation of individual tiles deforms the individual tiles and applies forces on neighboring tiles and external points of contact. Activating EAP tiles in a serial fashion can provide a waveform. For example, the following actions results in a waveform: activating EAP tiles 234, 256 in the +Z direction; deactivating EAP tiles 234, 256; activating EAP tiles 254, 224 in the +Z; and deactivating EAP tiles 254, 224. Activating groups of EAP tiles can provide raised formations. For example, activating EAP tiles 222, 244, 224, 254, 232, 246, 232, 234, 256 in the +Z direction results in a raised formation of EAP tiles. Those skilled in the art shall recognize that numerous other desired deformations and motions can be created using EAP tiles without departing from the scope or spirit of EAP braided structure 200.

Figure 3:
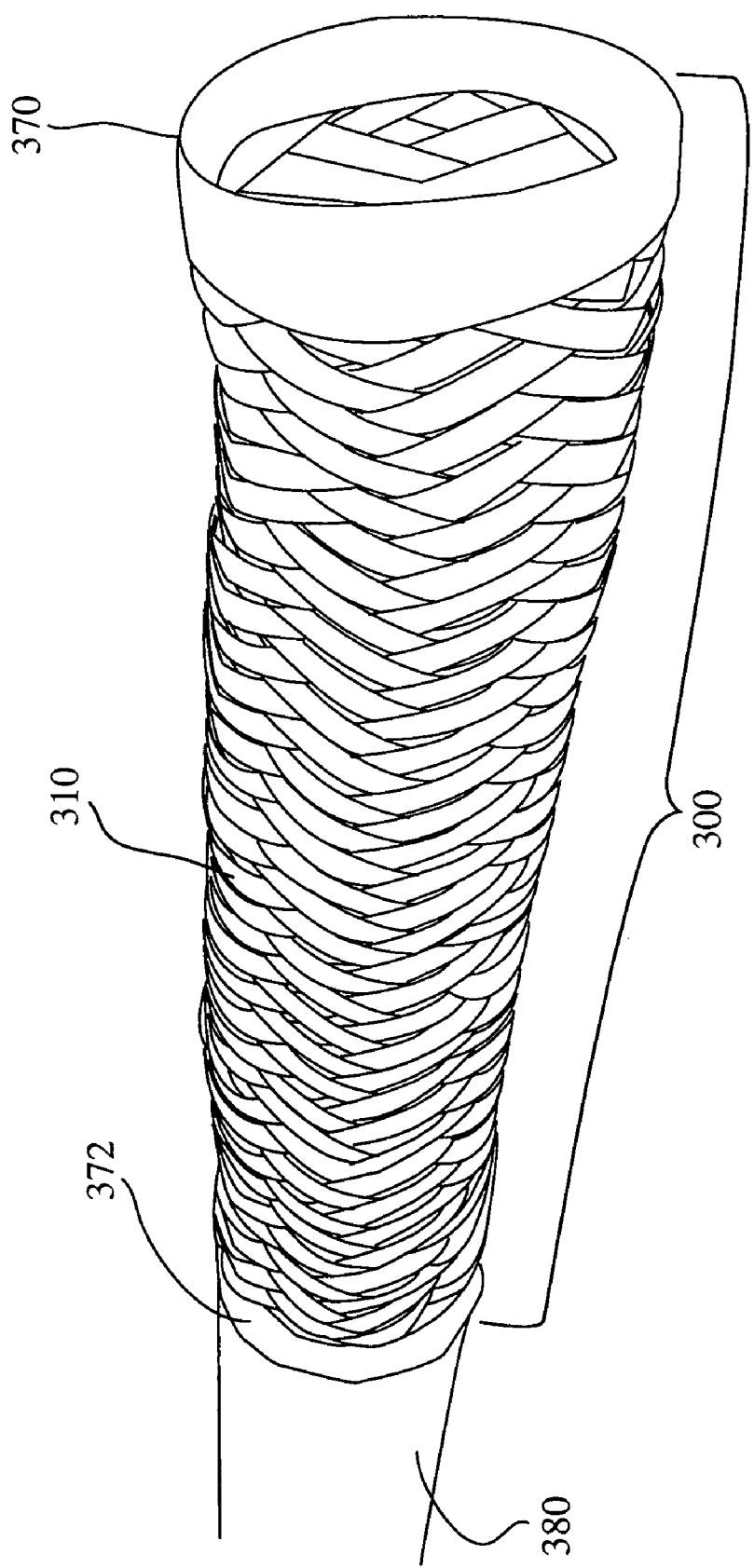
FIG. 3 is a perspective view of one embodiment of an EAP structure.

FIG. 3 is a perspective view of one embodiment of an EAP structure. The EAP biaxial braided structure of FIG. 3 has a configuration similar to a Chinese finger trap or a Chinese handcuff. As shown in FIG. 3, EAP biaxial braided structure 300 includes a plurality of EAP strands 310 having a biaxial braided configuration, an outer frame 370 and an inner frame connector 372. Outer frame 370 operatively couples the distal ends of the plurality of EAP strands 310 to each other. Inner frame connector 372 operatively couples rigid structure 380 and the proximal ends of the plurality of EAP strands 310 of EAP biaxial braided structure 300. Outer frame 370 and inner frame connector 372 can comprise an elastic or rigid material. In the embodiment of FIG. 3, outer frame 370 comprises a semi-elastic material. In one embodiment, the length (L) of each EAP strand 310 from proximal end to distal end is approximately equal and can be represented by the following Equation 1.

$$L=(0.5*C)/\cosine(A)$$ (Equation 1)

where

L=length of EAP strand

C=circumference of biaxial braided structure

A=braid angle

In one embodiment, EAP segments along each EAP strand 310 are distributed on a regular cycle so sinusoidal activations of any neighborhood of EAP segments will contribute to peak deflections anywhere on EAP biaxial braided structure 300. Those skilled in the art shall recognize that EAP biaxial braided structure 300 can include variations in braid angle and tightness of the braid to provide different braid characteristics and different braid behaviors when used as an artificial muscle without departing from the scope and spirit of EAP biaxial braided structure 300. Those skilled in the art shall recognize that EAP biaxial braided structure 300 can comprise other configurations without departing from the scope or spirit of the EAP biaxial braid structure 300. For example, EAP biaxial braided structure 300 can be unattached to rigid structure 380, which forms a snake-like structure.

Figure 4A:
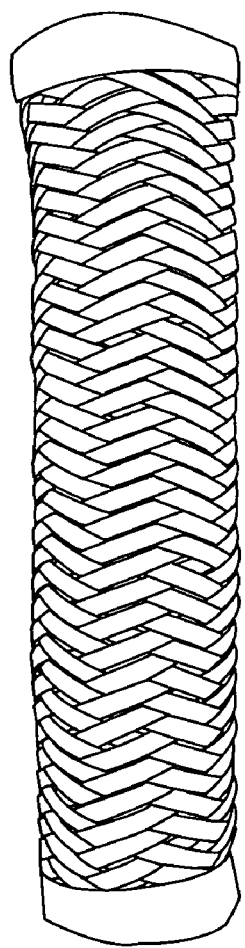
FIG. 4A is a side view of one embodiment of an EAP structure.
Figure 4B:
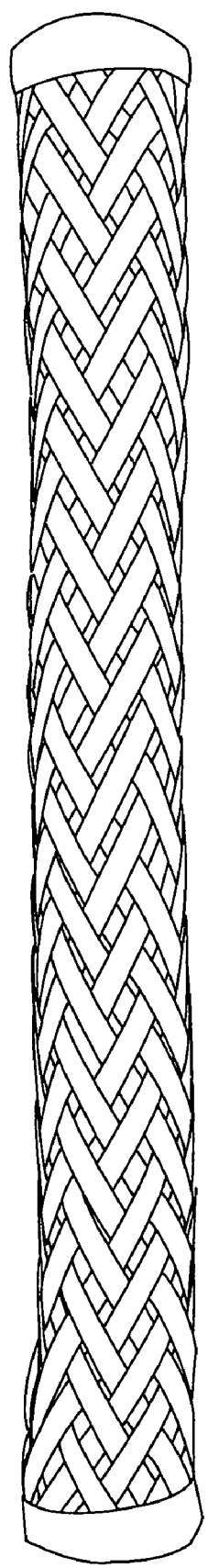
FIG. 4B is a side view of one embodiment of an EAP structure.

FIGS. 4A–4D are side views of one embodiment of an EAP structure depicting various desired deformations. FIG. 4A is a side view of one embodiment of an EAP structure depicting a contracted deformation. EAP braided biaxial structure 400 of FIG. 4A is substantially similar to EAP braided biaxial structure 300 of FIG. 3, and thus, similar components are not described hereinagain. As shown in FIG. 4A, EAP braided biaxial structure 400 retains its contracted biaxial structure because EAP segments are not activated. FIG. 4B is a side view of one embodiment of an EAP structure depicting an elongated deformation. As shown in FIG. 4B, EAP braided biaxial structure 400 has an elongated biaxial structure because all EAP segments are activated. FIG. 4C is a side view of one embodiment of an EAP structure depicting a curled deformation. As shown in FIG.

4C, EAP braided biaxial structure 400 has a curled structure because selected groups of EAP segments are activated. Specifically, groups of EAP segments along curve 482 are activated with a first polarity and groups of EAP segments along curve 484 are activated with a polarity opposite the first polarity. FIG. 4D is a side view of one embodiment of an EAP structure depicting a double-curled deformation. As shown in FIG. 4D, EAP braided biaxial structure 400 has a double-curled structure because selected groups of EAP segments are activated differentially. Specifically, groups of EAP segments along curve 492 and curve 498 are activated in similar fashion to curve 482 of FIG. 4C and groups of EAP segments along curve 494 and curve 496 are activated in similar fashion to curve 484 of FIG. 4C.

Figure 5:
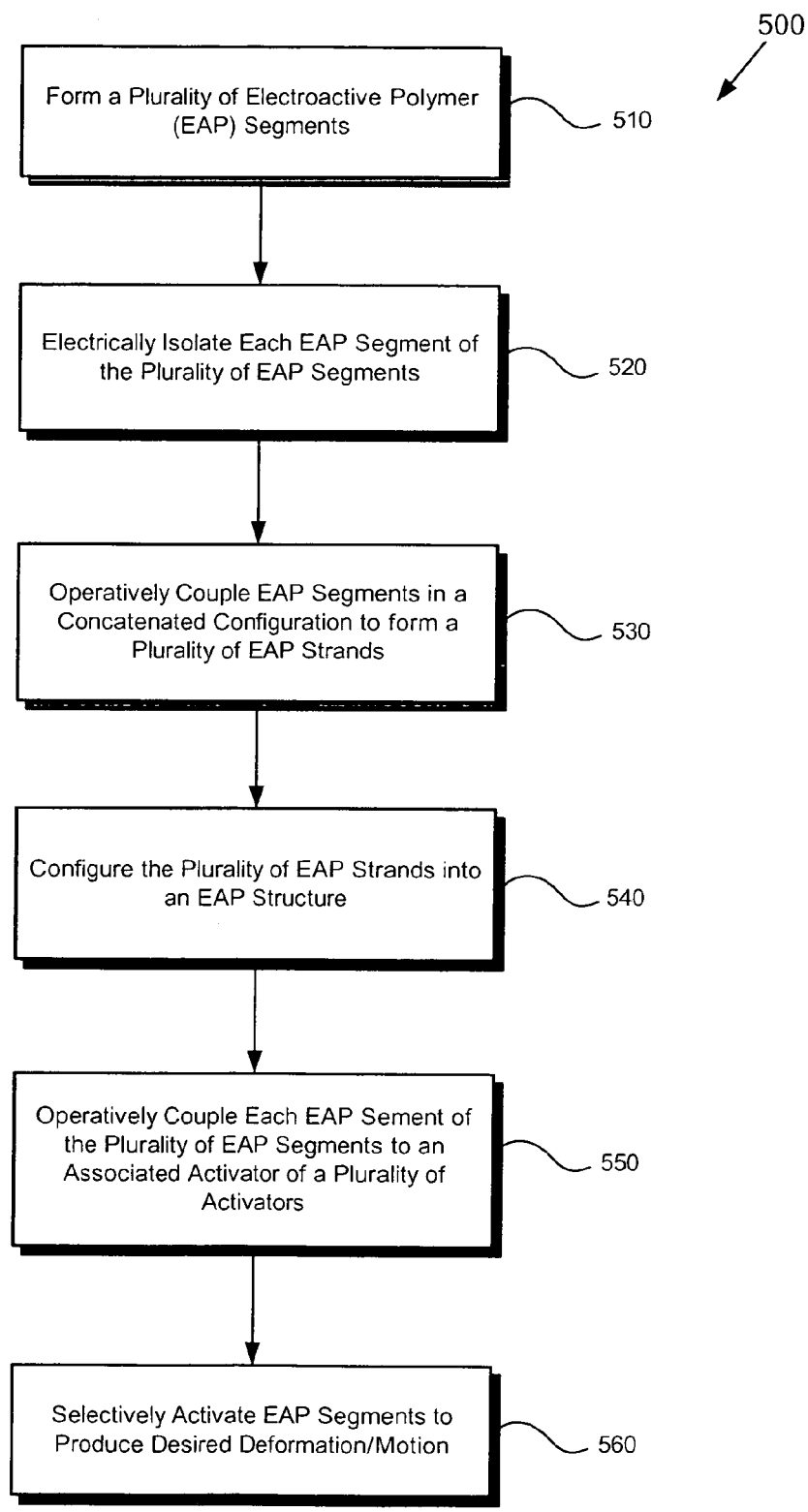
FIG. 5 is a flowchart of an exemplary method of one embodiment of an EAP structure.

FIG. 5 is a flowchart illustrating exemplary process steps taken to implement an exemplary EAP structure. Certain details and features have been left out of flowchart 500 of FIG. 5 that are apparent to a person of ordinary skill in the art. For example, a step may consist of one or more sub-steps or may involve specialized equipment or materials, as known in the art. While STEPS 510 through 560 shown in flowchart 500 are sufficient to describe one embodiment of the EAP structure, other embodiments of the EAP structure may utilize steps different from those shown in flowchart 500.

Referring to FIG. 5, at STEP 510 in flowchart 500, the method forms a plurality of EAP segments. In one embodiment, EAP segments have a tile configuration, where depth is less than width or length. After STEP 510, the method proceeds to STEP 520. At STEP 520 in flowchart 500, the method electrically isolates each EAP segment of the plurality of EAP segments formed in STEP 510. In one embodiment, the method uses insulators such as plastic to electrically isolate each EAP segment. After STEP 520, the method proceeds to STEP 530. At STEP 530 in flowchart 500, the method operatively couples EAP segments in a concatenated configuration to form a plurality of EAP strands. After STEP 530, the method proceeds to STEP 540.

At STEP 540 in flowchart 500, the method configures the plurality of EAP strands into an EAP structure. In one embodiment, the method configures the plurality of EAP strands into an EAP braided structure. In one embodiment, the method configures the plurality of EAP strands into an EAP biaxial braided structure. In one embodiment, the method configures the plurality of EAP strands into an EAP biaxial braided snake. In one embodiment, the method configures the plurality of EAP strands into an EAP braided sphere. In one embodiment, the method configures the plurality of EAP strands into an EAP braided disc. In one embodiment, the method configures the plurality of EAP strands into an EAP braided artificial muscle. In one embodiment, the method configures the plurality of EAP strands into an EAP braided regulator (e.g., artificial sphincter). In one embodiment, the method configures the plurality of EAP strands into an EAP braided peristaltic pump (e.g., artificial heart or colon). In one embodiment, the method configures the plurality of EAP strands into an EAP braided locally controllable bladder. After STEP 540, the method proceeds to STEP 550. At STEP 550 in flowchart 500, the method operatively couples each EAP segment of the plurality of EAP segments to an associated activator of a plurality of activators. In one embodiment, the plurality of activators comprises electrode pairs (e.g., first electrode and second electrode). In one embodiment, STEP 550 further includes a sub-step of operatively coupling the plurality of activators to a controller such as a computer to provide global and local activation of EAP segments. After STEP 550, the method proceeds to STEP 560. At STEP 560 in flowchart 500, the method selectively activates EAP segments to produce a desired deformation or motion. Those skilled in the art shall recognize that the order of some of the STEPS of the method in flowchart 500 can be changed without departing from the scope or spirit of the EAP structure. For example, STEP 550 can be performed subsequent to STEP 510 and prior to STEP 520.

From the above description, it is manifest that various techniques can be used for implementing the concepts without departing from their scope. Moreover, a person of ordinary skill in the art would recognize that changes can be made in form and detail without departing from the spirit and the scope. The described embodiments are to be considered in all respects as illustrative and not restrictive. It should also be understood that the particular embodiments described herein are capable of many rearrangements, modifications, and substitutions without departing from the scope and spirit.

We claim:

1. An EAP Structure, comprising:
 a) at least one EAP strand, wherein an EAP strand comprises:
  i) a plurality of EAP segments, wherein an EAP segment comprises:
   (1) an EAP tile having a length, a width and a depth, wherein said depth is less than said length and said width;
   (2) an activator, operatively coupled to said EAP tile, capable of facilitating activation of said EAP tile;
  ii) a plurality of insulators;
 wherein, said plurality of EAP segments and said plurality of insulators have a concatenated configuration, wherein adjacent EAP segments are electrically separated by one of said plurality of insulators, and wherein said EAP segments are operatively coupled to said plurality of insulators.

2. The EAP structure of claim 1, wherein said activator comprises a first electrode and a second electrode.

3. The EAP structure of claim 1, wherein said EAP tile comprises a conductive polymer.

4. The EAP structure of claim 1, wherein said EAP tile comprises a dielectric elastomer.

5. The EAP structure of claim 1, wherein said EAP structure further comprises a controller, operatively coupled to a plurality of said activators, capable of selectively activating said EAP tiles individually or in groups.

6. The EAP structure of claim 1, wherein said EAP structure comprises a plurality of EAP strands having a braided configuration.

7. The EAP structure of claim 1, wherein said EAP structure comprises a plurality of EAP strands having a configuration selected from the group consisting of EAP biaxial braided snakes, EAP braided spheres, EAP braided discs, EAP braided artificial muscles, EAP braided regulators, EAP braided peristaltic pumps and EAP braided locally controllable bladders.

8. The EAP structure of claim 1, wherein said EAP structure comprises a plurality of EAP strands having an EAP animal toy configuration comprising a plurality of discrete EAP structures, which can be activated independently or in conjunction.

9. The EAP structure of claim 6, wherein said EAP structure further comprises a frame, operatively coupled to ends of said plurality of EAP strands.

10. The EAP structure of claim 1, wherein said EAP structure comprises a plurality of EAP strands having a biaxial braided configuration.

11. The EAP structure of claim 10, wherein said EAP structure comprises a plurality of EAP strands having a length (L) in accordance with the following equation:

$$L = (0.5C)/\mathrm{cosine}(A)$$

where
  L=length of EAP strand
  C=circumference of biaxial braided structure
  A=braid angle.

12. The EAP structure of claim 10, wherein said EAP structure further comprises a rigid structure operatively coupled to said plurality of EAP strands having said biaxial braided configuration by an inner frame connector.

13. The EAP structure of claim 10, wherein EAP structure further comprises an outer frame operatively coupled to a distal end of said plurality of EAP strands having said biaxial braided configuration.

* * * * *